United States Patent

Berger

Patent Number: 6,133,334
Date of Patent: Oct. 17, 2000

[54] METHOD FOR INFLUENCING THE DISPERSIBILITY, EMULSIFIABILITY SOLUBILITY AND/OR REACTIVITY OF LOW MOLECULAR WEIGHT SOLIDS CONTAINING ALKYL GROUPS

[75] Inventor: Steffen Berger, Düsseldorf, Germany

[73] Assignee: Arplas Gesellschaft Fur Plasmatechnologie mbH, Germany

[21] Appl. No.: 08/913,603
[22] PCT Filed: Dec. 13, 1995
[86] PCT No.: PCT/EP95/04911
§ 371 Date: Feb. 27, 1998
§ 102(e) Date: Feb. 27, 1998
[87] PCT Pub. No.: WO96/19285
PCT Pub. Date: Jun. 27, 1996

[30] Foreign Application Priority Data

Dec. 22, 1994 [DE] Germany ............... 44 47 375

[51] Int. Cl.[7] .................................................. C08J 3/28
[52] U.S. Cl. ...................... 522/1; 204/168; 156/272.6
[58] Field of Search ................................ 204/167, 168; 156/272.6; 264/483, 83; 522/1

[56] References Cited

FOREIGN PATENT DOCUMENTS

| | | |
|---|---|---|
| 0 122 289 | 10/1984 | European Pat. Off. . |
| 0 593 988 A1 | 4/1994 | European Pat. Off. . |
| 41 41 805 A1 | 6/1993 | Germany . |
| 1 326 197 | 8/1973 | United Kingdom . |
| WO 95/03344 | 2/1995 | WIPO . |

OTHER PUBLICATIONS

Chemical Abstracts, 26473d., vol. 81, No. 6, Aug. 12, 1974.
Methoden Der Organischen Chemie (Houben–Weyl), p. 1576, 1975.
Kunststoff Taschenbuch, 25th Edition, pp. 258–259, 1992.

*Primary Examiner*—Randy Gulakowski
*Assistant Examiner*—Allan Olsen
*Attorney, Agent, or Firm*—Finnegan, Henderson, Farabow, Garrett & Dunner, L.L.P.

[57] ABSTRACT

A method for influencing the dispersibility, emulsifiability, solubility and/or reactivity of low molecular weight solids containing alkyl groups wherein low molecular weight solids containing alkyl groups are subjected to a plasma treatment in a frequency range of from 10 kHz to 10 GHz.

12 Claims, 1 Drawing Sheet

METHOD FOR INFLUENCING THE DISPERSIBILITY, EMULSIFIABILITY SOLUBILITY AND/OR REACTIVITY OF LOW MOLECULAR WEIGHT SOLIDS CONTAINING ALKYL GROUPS

BACKGROUND OF THE INVENTION

The invention relates to a method for influencing the dispersibility, emulsifiability, solubility and/or reactivity of low molecular weight solids containing alkyl groups and to chemically modified low molecular weight solids containing alkyl groups. By low molecular weight solids is meant compounds with less than1000 atoms.

It is known that low molecular weight solids containing alkyl groups, for example paraffins, fatty acids, fatty alcohols and fatty acid esters, can be used in many fields.

To this end, dispersions, emulsions or solutions, for example, are produced from the low molecular weight solids containing alkyl groups in many applications. A disadvantage in this case is that, depending on the proportion of alkyl groups in the low molecular weight solids containing alkyl groups, a different dispersibility, emulsifiability or solubility in polar liquids, for example water, is found. The capacity of the solids for being dispersed, emulsified or dissolved in liquids of this type decreases as the alkyl group content increases. In order to compensate for these disadvantages, it is known to use auxiliary chemicals, for example dispersion agents or emulsifiers. A further effect due to the relatively poor dispersibility, emulsifiability or solubility is that only a relatively low solids density can be achieved in the dispersions, emulsions or solutions when using the low molecular weight solids containing alkyl groups. In addition, the alkyl group content influences the reactivity of the respective low molecular weight solid containing alkyl groups. As a rule, its reactivity decreases as the alkyl group content increases. This limits the possible applications of the low molecular weight solids containing alkyl groups.

"Kunststoff-Taschenbuch", 25th Edition, pages 248 to 259 discloses a process for the after-treatment of solids containing alkyl groups. In this case, the surface of the solid containing alkyl groups, for example a PE surface, is treated using a high-voltage plasma, in order to achieve local chemical modification. The effect achieved as a result of this local surface treatment, for example in the case of shaped parts, is an improvement in the paintability or printability.

The object of the invention is to provide a method of the generic type, with which it is possible to influence dispersibility, emulsifiability, solubility and/or reactivity of low molecular weight solids containing alkyl groups in a simple and cost-effective fashion.

SUMMARY OF THE INVENTION

According to the invention, this object is achieved in that the low molecular weight solids containing alkyl groups are subjected to a plasma treatment in a frequency range of from 10 kHz to 10 GHz. It has surprisingly been found that, by the plasma treatment, a deliberate alteration of material properties can be brought about within the low molecular weight solids containing alkyl groups. In particular, the plasma treatment can be used to obtain chemical specialty products which can be used in a wide variety of ways. In addition, it is very advantageously possible to use the plasma treatment to influence dispersibility, emulsifiability or solubility in polar liquids of the low molecular weight solids containing alkyl groups. The plasma treatment produces the surprising effect that, depending on the alkyl group content in the low molecular weight solids containing alkyl groups, a deliberate improvement in dispersibility, emulsifiability, solubility and reactivity of the low molecular weight solids containing alkyl groups can be achieved. Higher solids densities in dispersions or emulsions can be achieved by virtue of this improved processability. Possibly occurring repulsive reactions between the individual particles of the low molecular weight solids containing alkyl groups in a dispersion or emulsion are deliberately reduced by the plasma treatment, so that a more uniform and denser solids distribution can be obtained. This substantially obviates the need to use aids such as dispersion agents or emulsifiers.

In an advantageous configuration of the invention, provision is made for the plasma treatment to be carried out with varying frequencies, preferably with combinations of varying frequencies of different value. It is thus possible, very advantageously, to carry out the plasma treatment with frequencies which can be switched on sequentially, with frequencies of different value which can be switched on alternately, with at least two frequencies of different value which can be switched on simultaneously, and frequency-switching combinations resulting from these. By means of this, it is very advantageously possible to adapt to the different chemical structure of the low molecular weight solids containing alkyl groups which are used, and their intended use after the plasma treatment.

In a further advantageous configuration of the invention, provision is made for the plasma treatment to be carried out while supplying at least one inert gas, for example helium and/or argon, and/or while supplying at least one reaction gas, for example oxygen and/or nitrogen and/or monomers. It is also preferable if the plasma treatment is carried out sequentially with an inert gas plasma and at least one reaction gas plasma and/or a reaction gas plasma mixture or while supplying a mixture of at least one inert gas and a reaction gas. By selecting for the process gas during the treatment a composition (inert gas, reaction gas, reaction gas mixture) which is tailored to the low molecular weight solids containing alkyl groups that are to be modified, it is possible to incorporate into the low molecular weight solids containing alkyl groups a sufficient quantity of the reactive groups, for example hydroxyl groups, carboxyl groups, primary and secondary amino groups, which are needed for the chemical modification. These incorporated groups are capable of reacting with the low molecular weight solid containing alkyl groups and forming chemical bonds and/or physically adhering to it. Further polar, but unreactive groups that can be incorporated, for example carbonyl groups or tertiary amino groups, can likewise bring about a change in the properties of the low molecular weight solids containing alkyl groups.

The low molecular weight solids containing alkyl groups which are treated have a relatively homogeneous distribution of the reactive or unreactive groups over the entire spatial extent of the low molecular weight solids containing alkyl groups. It is thus possible to obtain any type of low molecular weight solids containing alkyl groups, which after the plasma treatment are suitable for particular applications. A simple way of adjusting the low molecular weight solids containing alkyl groups to their special application is to carry out the plasma treatment according to the invention.

Overall, use has been made of the surprising effect of the invention that characteristics, such as molecular weight, have no significant influence on the degree of the effect obtained by means of the plasma treatment, but instead the alkyl group content and the particle size in the starting material are, primarily, decisive in this regard. Functional groups already present in the starting material have, surprisingly, no significant influence on the effect of the plasma treatment according to the invention. By selecting a composition for the process gases which is tailored to the chemical structure of the starting material, and a sequence of frequency combinations which, in particular, is tailored to this, it is possible to incorporate various functional groups in alignment with the final intended purpose, and the dispersibility, emulsifiability, solubility and reactivity to be obtained, and the dispersion media, emulsifying media and solvents used in connection with this.

DETAILED DESCRIPTION OF THE DRAWINGS

Figure 1:
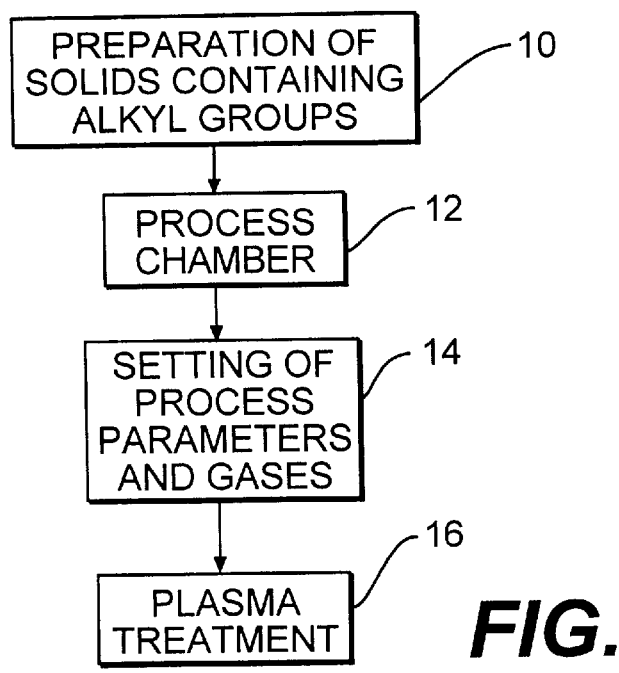
Figure 2:
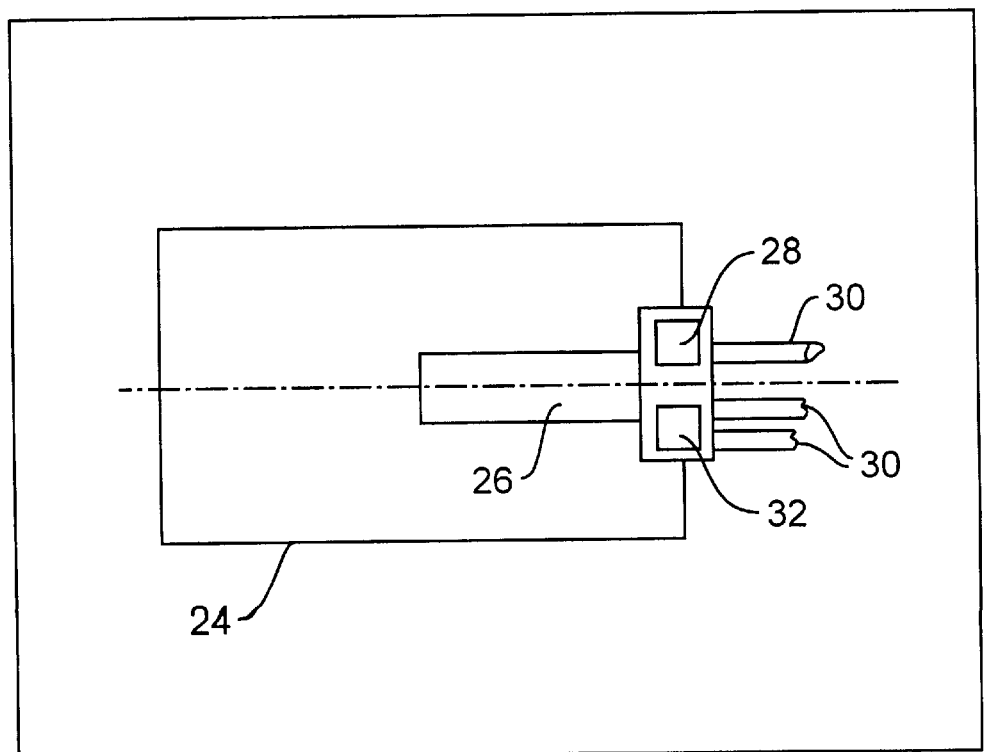

The invention will be explained in more detail below with reference to an illustrative embodiment and with the aid of the accompanying drawings, in which:

FIG. 1 shows, in a flow chart, a process sequence for treating low molecular weight solids containing alkyl groups, and FIG. 2 shows a schematic representation of an arrangement for carrying out the method.

DETAILED DESCRIPTION OF THE INVENTION

FIG. 1 is intended to illustrate the method according to the invention with the aid of a chart. A first step 10 involves preparation of the low molecular weight solids containing alkyl groups which are available as starting materials. In a next step 12, the prepared starting material is introduced into a process chamber. The process chamber may in this case, for example, be a rotary drum of a plasma furnace, known per se, for carrying out a plasma treatment.

In a next step 14, the process parameters and process gases desired for treating the starting material are set. In particular, this involves establishing the special combinations of the process gases, that is to say a first treatment with an inert gas plasma, preferably with helium and/or argon, and the subsequent treatment with a reaction gas plasma, preferably with oxygen and/or nitrogen and/or monomers, or alternatively the treatment with a plasma which is produced from a mixture of the abovementioned gases. In addition, the radio frequencies needed for plasma generation in a vacuum, and their timing, are set. Thus, variants may be envisaged, in which a plasma treatment is carried out firstly with a lower frequency, for example 13.56 MHz, and subsequently with a higher frequency, for example 2.45 GHz. Switching the frequencies on alternately may also be envisaged. Of course, other frequencies may also be set in arbitrary, freely selectable sequence in order to carry out the plasma treatment. It is also possible to provide alternating, and if appropriate even simultaneous, switching on of frequencies of different value. Further to this, the desired rotational speed of the rotary drum, for example in the region of between 4 and 20 revolutions per minute, and the desired process pressure which, for example, is in the range of between 0.1 mbar and 2 mbar, are set. During the plasma treatment, the process pressure may be subject to fluctuations associated with the method. The treatment duration, for which the treatment of the starting material takes place, is also established. It is, for example, between 5 and 900 s. The abovementioned process parameters, or process gases, can be varied relative to one another in combination and are, in particular, tailored to the composition of the starting material which is physically present in each case.

In a next step 16, the plasma treatment of the starting material with the process parameters, or process conditions, set in step 14 then takes place. In this case, it is likewise conceivable for the process parameters to be varied and/or adjusted, for example using a control system, during the plasma treatment in step 16. By virtue of the described combination of the process gases and the process parameters of the plasma treatment, it is possible to incorporate a sufficient amount of the reactive groups, as a function of the starting material used, this incorporation needed for the purpose of a subsequent use of the low molecular weight solids containing alkyl groups. If need be, the solids are also cooled during the plasma treatment, since they may have a relatively low melting point. This prevents the starting materials being converted into a melt, as a result of the heat developed during the plasma treatment.

The method according to the invention is not restricted to the treatment of a specific low molecular weight solid containing alkyl groups. Thus, it is possible to subject mixtures of various low molecular weight solids containing alkyl groups, in a selectable combination, to the plasma treatment. This can be done in simple fashion by mixing the various low molecular weight solids containing alkyl groups, for example present in granulate form, in particular quantities that can be selected respectively.

FIG. 2 schematically shows the structure of a device which can be used for the method. A plasma system, denoted overall by 22, has a rotary drum 24. The rotary drum 24 is used as a process chamber and may, for example, consist of a strong material such as aluminum or stainless steel. The process chamber can be sealed hermetically in order to generate a vacuum, there being no need to enter into further details regarding this here. The rotary drum 24 is assigned a device 26 that serves as a reactor and is coupled to a generator 28 for microwave plasma excitation and a radiofrequency feed 32. Feed lines 30 for supplying process gases are also provided.

The arrangement represented here is merely an example, and the invention does not relate in detail to the physical structure of the system. The method according to the invention can, of course, also be carried out with a similar device that implements the individual steps of the method.

The method according to the invention then proceeds as follows. The low molecular weight solid containing alkyl groups (if appropriate a mixture of different solids) which has been selected and prepared, is introduced into the rotary drum 24 and mixed therein thoroughly, in accordance with the selected speed of rotation and direction of rotation, which may also be chosen to alternate. The selected process gas, or process gas mixture, is supplied via the feed lines 30, and a plasma is generated in the reactor 26 by means of the generator 28. The plasma may in this case advantageously be generated by inputting microwave radiation at powers of between 200 and 1500 W (2.45 GHz). This being the case, the process gas or process gas mixture preferably has a process pressure of between 0.1 and 2 mbar. By means of the radiofrequency feed 32, a frequency of, for example, 13.56 MHz is applied and a plasma is generated. From the plasma that has been generated, activated particles impact on the starting material with which the rotary drum 24 is filled. This causes a structural change inside the starting material, that is to say the solid with which the drum is filled, consisting in the incorporation of polar groups (that contain oxygen and/or nitrogen). These polar groups include reactive groups (hydroxyl groups, carboxyl groups, primary and secondary amino groups) as well as unreactive groups (carbonyl groups, tertiary amino groups). Cross-linking does not take place. By corresponding alternating supply of different process gases via the feed lines 30, and different application of the frequencies by means of the generator 28, or the radiofrequency feed 32, it is possible to have an effect on different compositions of the solids.

In a concrete example, a fatty alcohol having a particle size of between 2 mm to 5 mm is introduced into the rotary drum 24. As process parometers, a process gas pressure of 0.7 mbar with a speed of rotation of the rotary drum 24 equal to 7 revolutions per minute is set. The power of the generator 28 is 1200 W, and that of the radiofrequency feed 32 is 600 W. Argon, oxygen and nitrogen are supplied as process gases, and the starting substance which has been introduced is plasma-treated for a duration of 300 s overall. In detail, a treatment is carried out with an argon plasma for 30 s under radiofrequency excitation, and 30 s under microwave excitation, with an oxygen plasma for 60 s under radiofrequency excitation and 60 s under microwave excitation, and with a nitrogen plasma for 60 s under radiofrequency excitation and 60 s under microwave excitation. The generator 28 in this case produces a frequency of 2.45 GHz and the radiofrequency feed 32 produces a frequency of 13.56 MHz.

After the plasma treatment had finished, it was possible to establish, by comparative observation, that for the fatty alcohol which had been treated, the values of both the polar and the disperse components of the interfacial energy were, for the fatty alcohols that had been plasma-treated according to the invention, up to twice as high as those for the untreated fatty alcohols, depending on the temperature at which the measurement was taken. There was also a shift in the isoelectric point to a higher pH value.

What is claimed is:

1. A method for influencing the dispersibility, emulsifiability, solubility and/or reactivity of low molecular weight solids containing alkyl groups, comprising subjecting at least one low molecular weight solid containing alkyl groups to a plasma treatment carried out at a varying frequency in a frequency range of from 10 kHz to 10 Ghz.

2. A method for influencing the dispersibility, emulsifiability, solubility and/or reactivity of low molecular weight solids containing alkyl groups comprising subjecting at least one low molecular weight solid containing alkyl groups to a plasma treatment carried out with a combination of at least two frequencies of different value that vary in a frequency range of from 10 kHZ to 10 Ghz.

3. The method of claim 1 or 2, wherein the plasma treatment is carried out while supplying at least one inert gas.

4. The method of claim 3, wherein the inert gas is selected from the group consisting of helium and argon.

5. The method of claim 1 or 2, wherein the plasma treatment is carried out while supplying at least one reaction gas.

6. The method of claim 5, wherein the reaction gas is selected from the group consisting of oxygen, nitrogen.

7. The method of claim 1 or 2, wherein the plasma treatment is supplied sequentially with at least one inert gas plasma followed by at least one reaction gas plasma or a reaction gas mixture plasma or is supplied with a mixture of at least one inert gas and at least one reaction gas.

8. The method of claim 1 or 2, wherein the plasma treatment is supplied alternately with at least one inert gas plasma, at least one reaction gas plasma and at least one mixture of an inert gas/reaction gas plasma.

9. The method of claim 1 or 2, wherein the plasma treatment takes place at a process pressure of from 0.1 mbar to 2 mbar.

10. The method of claim 1 or 2, wherein the duration of the plasma treatment is between 5 seconds and 900 seconds.

11. The method of claim 1 or 2, wherein the low molecular weight solid containing alkyl groups is mixed or stirred during the plasma treatment.

12. The method of claim 1 or 2, wherein the low molecular weight solid containing alkyl groups is a fatty alcohol.

* * * * *